United States Patent [19]

Bartha et al.

[11] 3,959,127

[45] May 25, 1976

[54] BIODEGRADATION OF OIL ON WATER SURFACES

[75] Inventors: Richard Bartha, East Brunswick, N.J.; Ronald M. Atlas, Louisville, Ky.

[73] Assignee: The United States of America as represented by the Secretary of the Navy, Washington, D.C.

[22] Filed: Mar. 13, 1975

[21] Appl. No.: 558,040

Related U.S. Application Data

[63] Continuation-in-part of Ser. No. 421,874, Dec. 5, 1973, abandoned.

[52] U.S. Cl. ................................... 210/11; 210/36; 210/40; 71/64 F; 195/3 H; 210/DIG. 27
[51] Int. Cl.² .......................................... C02B 9/02
[58] Field of Search ............ 210/11, 2, 12, DIG. 21, 210/36, 40; 71/86, 64 F, 64 C, 8, 9; 260/933; 195/3 H, 96, 100

[56] References Cited
UNITED STATES PATENTS

| | | | |
|---|---|---|---|
| 3,205,061 | 9/1965 | Mason, Jr. | 210/64 F |
| 3,607,741 | 9/1971 | Sohnius | 210/36 |
| 3,714,063 | 1/1973 | Salomone | 210/11 |
| 3,728,208 | 4/1973 | Whittington et al. | 210/36 |
| 3,729,410 | 4/1973 | Abadie et al. | 210/40 |
| 3,769,164 | 10/1973 | Azarowicz | 210/11 |

Primary Examiner—Charles N. Hart
Assistant Examiner—Benoit Castel
Attorney, Agent, or Firm—R. S. Sciascia; L. I. Shrago; C. E. Vautrain, Jr.

[57] ABSTRACT

Free-floating oil slicks on bodies of sea and fresh water are disposed of by microbial degradation at a greatly enhanced rate by applying the essential microbial nutrients, nitrogen and phosphorus, to the oil slick in a form that dissolves in or adheres to the oil and thus selectively stimulates the activity of oil-metabolizing microorganisms.

1 Claim, 1 Drawing Figure

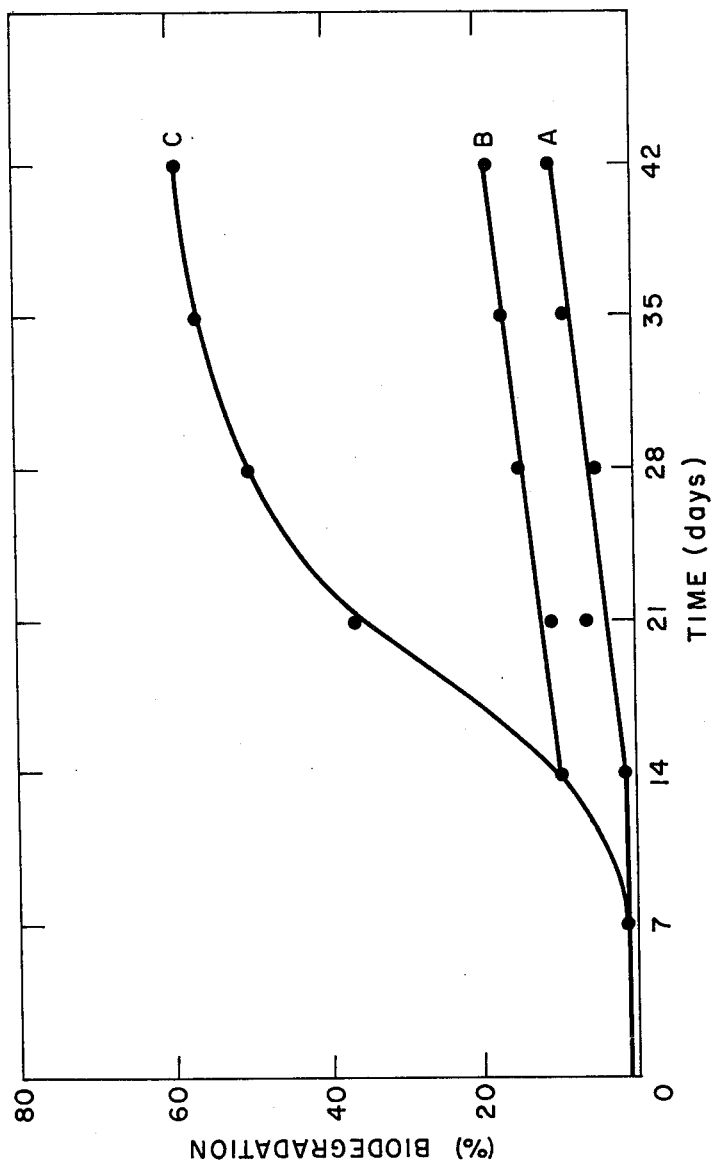

BIODEGRADATION OF OIL ON WATER SURFACES

This application is a continuation-in-part of our copending application, Ser. No. 421,874, filed Dec. 5, 1973 and having the same title, now abandoned.

This invention relates to the removal of polluting oil from the surface of salt or fresh water and, more particularly, to such removal by artificially increasing the rate of natural oil-degrading activity of microorganisms through providing essential nutrients to the microorganisms that are active in oil degradation.

The process of the present invention has special advantage under adverse conditions of weather, currents, or tides that render alternate methods of oil removal partially or completely ineffective.

The oil pollution of natural bodies of water and especially that of the ocean has caused increasing problems and public concern. The increasing frequency of oil spill incidents is caused by routine operations and/or accidents that accompany the largescale transportation of petroleum by water and the drilling for oil on the continental shelfs. The inappropriate disposal of residual oils represents another substantial source of oil pollution. Oil spills cause extensive economic and ecological damage by fouling of recreational beaches, boats, fishing gear, and harbor installations, and by destroying or tainting many forms of aquatic life. The cleanup of accidentally spilled oil from water surfaces is a technically difficult and very expensive process, and some cleanup techniques tend to inflict additional damage on the environment. The currently available cleanup techniques fall into the following categories: (1) physical removal, with or without the use of absorbents, (2) dispersion with detergents, (3) sinking, and (4) burning. Physical removal is the most desirable remedy, but is feasible only under ideal weather conditions and if the oil can be effectively prevented from spreading by the use of floating booms. Since seas higher than 1–2 feet and currents in excess of 2–3 knots render floating booms ineffective, this technique has had very limited success on the open ocean. Dispersion of oil has detrimental side effects because of detergent toxicity and by bringing oil droplets in contact with organisms that live on the ocean floor and in the water column. Sinking has similar side effects, and retards the ultimate degradation of oil by incorporating it into largely anaerobic sediments. Burning is possible by use of wicking agents only. This approach is restricted by safety considerations, by the incomplete burning of the oil, and by the resulting air pollution problem.

Polluting oil left to its natural fate is eventually consumed by microorganisms that use it as a source of carbon and energy. This natural biodegradation of the polluting oil is a slow process, and is consequently unable to prevent the oil from causing extensive damage before its ultimate elimination. The present invention describes a way to speed up this natural biodegradation process to a level that allows its use as a novel oil cleanup process and technique.

Accordingly, it is an object of the present invention to provide a process for removing polluting oil from a salt or fresh water surface which is effective notwithstanding sea and weather conditions.

Another object of this invention is to provide a process for removing polluting oil from water surfaces which avoids detergent toxicity and undesirable contact of oil droplets with organisms that live on the ocean floor and in the water column.

A further object of this invention is to provide a process for removing polluting oil from water surfaces which accelerates natural biodegradation processes and avoids air and water pollution.

Other objects, advantages and novel features of the invention will become apparent from the following detailed description thereof when considered in conjunction with the accompanying drawing the single FIGURE of which graphically illustrates the effectiveness of the process.

The present invention, in general, provides for the removal of free-floating oil slicks on bodies of sea- and fresh water by microbial degradation at a far greater rate than normally occurs in these environments. This greatly enhanced rate of oil degradation is accomplished by applying the essential microbial nutrients to the oil slicks in a form that dissolves in or adheres to the oil and thus selectively stimulates the activity of oil-metabolizing microorganisms.

For maximum proliferation and metabolic activity, hydrocarbon degrading microorganisms require additional nutrients such as nitrates and phosphates. These are absent from oil and are typically present in natural waters in limiting amounts only. The following experiments demonstrate that natural oil biodegradation can be greatly stimulated by the addition of these salts.

EXPERIMENT 1

In this experiment 1 ml Sweden crude oil was added to 100 ml fresh seawater containing its natural microbial population, and was incubated in the laboratory with agitation at 28°C. Only 5% of this oil was biodegraded in 18 days. Addition of 101 mg $KNO_3$, 10 mM, in combination with 7.5 mg $Na_2HPO_4$, 0.5 mM, increased the biodegradation of the petroleum during the same time period to 70%.

These salts are, however, highly water soluble and, therefore, of use only in an enclosed environment. For use on oil that floats on an essentially infinite volume of water as in the case of an oceanic oil spill, sources of nitrogen and phosphorous were required that dissolved in or adhered to the floating oil rather than being diluted or dispersed in the water.

EXPERIMENT 2

The procedure of experiment 1 was repeated using various oleophilic sources of nitrogen and phosphorous as substitutes for nitrate and phosphate salts. As before, these substances were applied at 10 mM and 0.5 mM concentration of nitrogen and phosphorous, respectively. The combination of 62 mg of Sun Oil CRNF, a paraffinized urea slow-release garden fertilizer, nitrogen content 26.8%, manufactured by the Sun Oil Company, and 7 mg of pyrophosphoric acid dioctyl ester, also referred to as octylphosphate, manufactured by the Stauffer Chemical Co., supported petroleum biodegradation at a level equal to or better than that described for the nitrate and phosphate salts, i.e. 70% of the total weight or higher.

Application of nitrogen and phosphorous fertilizers to natural bodies of water may be objected to on the ground that they may cause algal blooms. The following experiment demonstrates that neither Sun Oil CRNF nor pyrophosphoric acid dioctyl ester trigger algal blooms since the nitrogen and phosphorous provided in this form are apparently not available for algal metabolism.

EXPERIMENT 3

Freshly collected 150 ml samples of seawater were either left untreated, were treated with a combination of Sun Oil CRNF and pyrophosphoric acid dioctyl ester, 10 mM and 0.5 mM for nitrogen and phosphorous, respectively, or were treated with a combination of 10 mM $KNO_3$ and 0.5 mM $Na_2HPO_4$. All samples were incubated under continuous fluorescent light, intensity 220 foot candles at 20°C for 60 days. Algal development was measured by the chlorophyll content of the samples. Chlorophyll was below detection limit, less that 0.0033 $\mu$g/ml, in the untreated and the Sun Oil CRNF plus pyrophosphoric acid dioctyl ester treated flasks. In contrast, chlorophyll rose in the $KNO_3$ plus $Na_2HPO_4$-treated flasks to 0.15$\mu$g/ml.

EXPERIMENT 4

Since the previous experiments were conducted in enclosed systems, the invention's suitability for the treatment of free-floating oil slicks will now be considered. To demonstrate this capability under controlled conditions, miniature, 1 ml, slicks of Sweden crude oil were floated on 113 l seawater tanks. The individual miniature oil slicks were confined each to a 9.6 $cm^2$ surface area by floating glass frames. Fresh seawater was continuously pumped through these tanks at the rate of 450 l per day. Some of the 1 ml oil slicks were left untreated, others were treated with Sun Oil CRNF, 62 mg, and pyrophosphoric acid dioctyl ester, 7 mg, and a third set was treated with $KNO_3$, 101 mg, plus $Na_2HPO_4$, 7.5 mg. The biodegradation of the oil slicks was monitored for 42 days. During this period, the seawater temperature gradually rose from an initial 15°C to a final 20°C. In weekly intervals some of the miniature slicks were retrieved and were analyzed for residual oil. The results were corrected for evaporation losses, and precautions were taken to assure that no oil was lost through escape from the containment. The single FIGURE of the drawing depicts the time-course of the biodegradation of the miniature oil slicks if left untreated, A, if treated with phosphate and nitrate salts, B, and if treated with Sun Oil CRNF and pyrophosphoric acid dioctyl ester, C. While only 10% of A and 18% of B were biodegraded, 60% of C was eliminated during the same experimental period. This experiment clearly establishes that suitable oleophilic, i.e. oil-seeking, sources of nitrogen and phosphorous greatly accelerate the natural biodegradation rate of free-floating oil slicks, and demonstrates the usefulness of the invention for the cleanup of free-floating oil.

Polluting petroleum hydrocarbons may be removed from bodies of water by means of the accelerated microbial degradation described using a variety of compounds and materials. The sources of nitrogen and phosphorous which are oleophilic by their chemical nature may be but are not limited to those that contain as part of their molecular structure aliphatic alicyclic, aromatic and heterocyclic hydrocarbon moieties of sufficient size to impart the compound with overall nonpolar and oleophilic properties. Pyrophosphoric acid dioctyl, phosphorous acid monoisoctyl ester and dodecylurea are examples of compounds of this class. All these compounds were tested and found to promote oil biodegradation. These sources may also be selected from compounds taken from the group including alkanes, cycloalkanes, and aromatic hydrocarbons substituted with amino, nitrosamin, nitro, nitrilo, carbamate acid urea groups or with any combination of the above listed substituents.

The process of the invention may also be practiced by using sources of nitrogen and phosphorous that are not oleophilic by their chemical nature but are rendered oleophilic by coating or microencapsulation with an oleophilic material or are rendered oleophilic by adsorption onto or mixing with an oleophilic carrier material. Materials that can be used as coating, microencapsulation, admixing and adsorbing agents to render oleophilic such sources of nitrogen and phosphorous that are polar and water-soluble by their chemical nature include but are not restricted to paraffin and other petroleum fractions, individual hydrocarbons, polyolefin, polyvinyl chloride, polyacrylamide, and polystyrene, polycarbamate among other synthetic polymers; fatty acids, alcohols and esters of sufficient carbon chain length as well as silicon polymers and elemental sulfur. These sources may also be selected from compounds taken from the group including monoalkyl, dialkyl, and trialkyl esters of phosphoric acid, hypophosphoric acid, phosphoric acid and pyrophosphoric acid, or from cycloalkyl and aryl groups substituted for some or all of the alkyl groups in the esters. Sun Oil CRNF, paraffinized urea, is an example of this class of compounds.

The process for removing petroleum hydrocarbons from bodies of water by stimulating the proliferation and activity of naturally present hydrocarbon-degrading microorganisms may also be accomplished by adding to the pollutants sources of nitrogen and phosphorous that are rendered oleophilic by coating or microencapsulation with materials from the class including paraffin wax, individual or mixed hydrocarbons, fatty acids, alcohols and esters each having carbon atoms in excess of six but fewer than 30 per molecule.

The invention may further be practiced by the use of materials which may or may not contain additional microbial nutrients such as carbohydrates, proteins, protein hydrolyzates, amino acids, chelated iron and vitamins, microbial inocula such as fresh, dried, freeze-dried or otherwise preserved cultures of oil-degrading microorganisms, dispersants such as ionic or nonionic detergents, absorbents such as straw, plastic foams, fired silica, vermiculite, perlite, etc., or sinking agents such as siliconized sand, ground chalk, etc. notwithstanding the type of mechanical equipment, e.g. sprayer, spreader, or other, that is used for the delivery of the formulation onto the oil slick.

What is claimed is:

1. A process for removing polluting petroleum hydrocarbons from bodies of water by rendering them degradable to microorganisms indigenous to natural waters comprising:

stimulating the proliferation and activity of said hydrocarbon degrading microorganisms by adding to the hydrocarbons sources of nitrogen and phosphorous having a strong affinity for oils, said sources being, respectively, a paraffinized urea slow-release garden fertilizer with a nitrogen content of substantially 25% and pyrophosphoric acid dioctyl ester in a substantially 9 to 1 ratio of fertilizer to ester.

* * * * *